United States Patent [19]
Berg et al.

[11] 3,991,052
[45] Nov. 9, 1976

[54] ANTIBIOTIC A-30641

[75] Inventors: David H. Berg, Greenfield; Robert L. Hamill, New Ross; Marvin M. Hoehn, Indianapolis, all of Ind.

[73] Assignee: Eli Lilly and Company, Indianapolis, Ind.

[22] Filed: July 18, 1975

[21] Appl. No.: 597,047

[52] U.S. Cl. .............................. 260/243 R; 195/81; 424/246
[51] Int. Cl.² ....................................... C07D 285/00
[58] Field of Search ............................... 260/243 R

[56] References Cited
OTHER PUBLICATIONS

Bell, et al., *J. Amer. Chem. Soc.*, vol. 80, 1001 (1958).
Hodges, et al., *Chem. Ind.* (London), 42–43 (1963).
Nagarajan, et al., *J. Amer. Chem. Soc.*, vol. 90, pp. 2980–2982 (1968).
Hauser, et al., *Helv. Chim. Acta*, vl. 53, pp. 1061–1073 (1970).
Minato, et al., *Chem. Commu.* 1971, pp. 44–45.
Argoudelis, et al., *J. Antibiot.*, vol. 24, pp. 383–389 (1971).
Kato, et al., *J. Antibiot.*, vol. 22, pp. 322–326 (1969).
Safe, et al., *J. Chem. Soc.*, Perk Trans., vol. 1, pp. 472–479 (1972).
Michel, et al., *J. Antibiot.*, vol. 27, pp. 57–64 (1974).
McCorkindale, et al., *Tetrahedron letters*, 1968, pp. 727–730.
Kato, et al., *Chem. Commun.* 1971, 1561–1562.
Yoshikoshi, *Chem. Abstr.* vol. 79, entry 66337c.

*Primary Examiner*—John M. Ford
*Attorney, Agent, or Firm*—Nancy J. Harrison; Everet F. Smith

[57] ABSTRACT

Antibiotic A-30641, a new epidithiodiketopiperazine antifungal agent, is produced together with canadensolide in the A-30641 antibiotic complex by submerged aerobic fermentation of *Aspergillus tamarii* NRRL 8101.

1 Claim, No Drawings

ANTIBIOTIC A-30641

BACKGROUND OF THE INVENTION

1. Field of the Invention

There is a continuing need for new, improved antifungal agents. Because there are wide variations in susceptibility among organisms, even organisms in the same or related species, there is a need for a wise variety of antifungal agents. In addition, individual patient reactions, the nature of the illness being treated, hypersensitivity, and the like, require that a variety of drugs be available for treatment. Improved agents of varying scope, therefore, are always welcomed by the medical practitioner.

2. The Prior Art

Antibiotic A-30641 is the major component of the A-30641 antibiotic complex. Spectral properties of antibiotic A-30641 indicate that it contains a dithiodiketopiperazine moiety. Other naturally-produced compounds containing this moiety include gliotoxin, sporidesmin, aranotin, chaetocin, verticillin, melinaceidin, oryzachlorin, chaetomin, and a metabolite form Penicillium turbatum [K. Michel et al., J. Antibiot, 27, 57 (1974)]. Antibiotic A-30641 differs from these compounds and is the first dithiodiketopiperazine which is characterized by the structural feature of a dihydro-1,2-oxazine ring in a tricyclic system.

Canadensolide is the other component of the A-30641 antibiotic complex. Although canadensolide is a known antifungal agent, it differs chemically from antibiotic A-30641 in that it does not contain a dithiodiketopiperazine moiety.

SUMMARY OF THE INVENTION

This invention relates to a novel antibiotic substance. In particular, this invention relates to a new dithiodiketopiperazine antibiotic arbitrarily designated herein as antibiotic A-30641.

This invention further relates to a process for producing antibiotic A-30641 and canadensolide by culturing a newly-characterized strain of Aspergillus tamarii, NRRL 8101, under submerged aerobic fermentation conditions until a substantial amount of antiobiotic activity has been produced. Antibiotic A-30641 and canadensolide are co-produced as an antibiotic complex designated herein as the A-30641 antibiotic complex.

The term "antibiotic complex" as used in the fermentation art and in this specification refers to a mixture of co-produced antibiotics. As will be recognized by those familiar with antibiotic production by fermentation, the ratio of antibiotics produced in an antibiotic complex will vary, depending on the fermentation conditions used.

The A-30641 antibiotic complex is isolated from the fermentation broth as an amorphous solid by extraction and adsorption techniques. Antibiotic A-30641 and canadensolide are isolated from the A-30641 antibiotic complex by chromatographic procedures. Antibiotic A-30641 is a useful antifungal agent.

DETAILED DESCRIPTION OF THE INVENTION

Antibiotic A-30641 is the major metabolite produced by the new Aspergillus tamarii strain NRRL 8101. Antibiotic A-30641 is, therefore, the major component of the A-30641 antibiotic complex.

Antibiotic A-30641 is an amorphous, colorless material which melts at about 160°–172° C. (decomp.).

Elemental analysis of antibiotic A-30641 gave the following results:

Calculated for $C_{12}H_9N_2O_5S_2Cl$: C, 39.95; H, 2.51; N, 7.56; O, 22.17; S, 17.77; Cl, 9.83; Found: C, 40.29; H, 2.72N, 7.67; O, 21.48; S, 17.86; Cl, 9.54.

The empirical formula of antibiotic A-30641 is $C_{12}H_9N_2O_5S_2Cl$. The apparent molecular weight of antibiotic A-30641 as determined by high-resolution mass spectrometry is in agreement with this formula: $M^+$, calculated for $C_{12}H_9N_2O_5S_2Cl$: 359.9642; found: 359.9670.

The infrared absorption spectrum of antibiotic A-30641 in chloroform has the following significant absorption maxima: 3450 (OH), 1730 ($>C=O$), 1630 (amide), 1490, 1450, 1350, 1185, 1150 and 1050 $cm^{-1}$.

The specific rotation of antibiotic A-30641 is $+73°$ ($c=1$, MeOH) when determined at a temperature of 26° C.

The proton magnetic resonance (pmr) spectrum of antibiotic A-30641 in deuterated chloroform has the following characteristics: $\delta$ 3.95 ($s$), 4.88 ($d$, J = 1.2 Hz), 5.15 (d, J = 5Hz), 6.20 ($s$, OH), 6.75 (s), 7.12 ($d$, J = 1.2 Hz), and 7.64 ($d$, J = 5Hz) ppm. On $D_2O$ shake, the singlet at 6.20 and the doublet at 7.64 are lost; and the doublet at 5.15 becomes a singlet.

Antibiotic A-30641 gave the following fragments on high-resolution mass spectrometry:

| Elemental composition | Calcd. | Found |
| --- | --- | --- |
| $C_{12}H_9N_2O_5S_2Cl$ | 359.9642 | 359.9670 |
| $C_{12}H_9N_2O_5Cl$ | 296.0200 | 296.0178 |
| $C_{10}H_8NO_4Cl$ | 241.0142 | 241.0138 |
| $C_{10}H_6N_2O_2Cl$ | 221.0118 | 221.0120 |
| $C_9H_4NO_3Cl$ | 208.9880 | 208.9890 |
| $C_8H_5NO_2Cl$ | 182.0008 | 182.0005 |

The following structure (I) has been proposed for antibiotic A-30641:

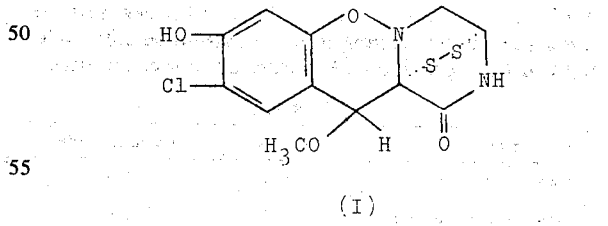

(I)

Antibiotic A-30641 can be acetylated in a conventional manner, using acetic anhydride and pyridine. The O-acetyl derivative of antibiotic A-30641 has an apparent molecular weight of 402 as determined by high-resolution mass spectrometry. The remainder of the mass spectrum of the acetyl derivative is identical to that of antibiotic A-30641. The pmr spectrum of the acetyl derivative lacks the resonance at $\delta$ 6.20 ppm (OH) and has an additional resonace at $\delta$ 2.34 ppm.

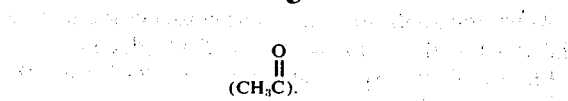

Of the prior-art dithiodiketopoperzines earlier discussed, oryzachlorin is believed to be most closely related to antibiotic A-30641 of this invention. The infrared absorption spectra and proton magnetic resonance spectra of oryzachlorin and antibiotic A-30641 are quite similar. The mass spectrum of oryzachlorine, however, confirms that it has a much higher molecular weight than does antibiotic A-30641.

Canadensolide, the other metabolite produced by the new *Aspergillus tamarii* strain NRRL 8101, was first reported by N. J. McCorkindale et al., *Tetrahedron Lett.* 1968, 727–730, as a metabolite of the fungus *Penicillium canadense*.

The stereochemistry of the structure proposed for canadensolide by McCorkindale et al. was later corrected by M. Kato et al., *Chem. Commun*, 1971, 1561–1562. The structure proposed by Kato et al. for canadensolide (II) is the following:

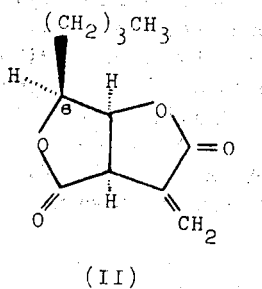

(II)

Recently, A. Yoshikoshi [Japan Kokai 73 40,797 (*Chem. Abstr.* 79: 66337c)], now calling the compound of structure II "6-epicanadensolide", provided a synthetic method for its preparation.

This invention provides a new method for producing canadensolide, the compound of formula II, by fermentation of *Aspergillus tamarii* NRRL 8101.

In Table I are given the $R_f$ values of antibiotic A-30641 and canadensolide in two thin-layer chromatographic systems on silica gel plates (precoated TLC Plates, silica gel 60 F-254, E. Merck, Darmstadt). The antibiotics were detected by 1) visual observation of fluorescence quenching under short-wave ultraviolet light and 2) spraying with iodine-azide spray reagent.

Table I

| Solvent System | A-30641 | Canadensolide |
| --- | --- | --- |
| Benzene:ethyl acetate (1:1) | 0.31 | 0.44 |
| Chloroform:acetone (3:2) | 0.42 | 0.56 |
| Ethyl acetate:chloroform (3:1) | 0.39 | 0.54 |

The $R_f$ values of antibiotic A-30641 and canadensolide in various paper-chromatographic systems, using *Klebsiella pneumoniae* bioautography, are given in Table II.

Table II

| Solvent System | A-30641 | Canadensolide |
| --- | --- | --- |
| Water saturated with butanol | 0.33 | 0.45 |
| Propanol:water (1:9) | 0.56 | 0.73 |
| Methanol:propanol:water (6:2:1) (paper buffered with 0.75 M $KH_2PO_4$ at pH 4.0) | 0.69 | 0.81 |
| Methyl ethyl ketone:benzene:$H_2O$ (1:5:1), upper layer | 0.83 | 0.91 |
| Methanol:0.05 M sodium citrate at pH 5.7 (7:3) (paper buffered with 0.05 M Na citrate at pH 5.7) | 0.76 | 0.87 |

Antibiotic A-30641 and canadensolide are co-produced by culturing a new strain of *Aspergillus tamarii* under submerged aerobic conditions in a suitable culture medium until a substantial amount of antibiotic activity is produced.

The microorganism useful for the preparation of antibiotic A-30641 and canadensolide was obtained from a soil sample from Curacao, the Netherlands Antilles. The A-30641-producing organism has been taxonomically classified as a new strain of *Aspergillus tamarii Kita* which is in the *Aspergillus flavus-oryzae* form group. The genus *Aspergillus* is described by K. B. Raper and D. I. Fennell in "The Genus Aspergillus," The Williams and Wilkins Co., Baltimore, Md., 1965. The following paragraphs summarize the observed characteristics of the A-30641-producing culture upon which the classification is based:

Color-code designations "ISCC-NBS" refer to those described in "The ISCC-NBS Method of Designating Colors and a Dictionary of Color Names", National Bureau of standards, Circular 553, U.S. Govt. Printing Office, 1955. Color-code designations "M&P" refer to those described by A. Maerz and M. Rea Paul in "A Dictionary of Color", McGraw-Hill Book Company, Inc., New York N. Y., 1950.

The A-30641 -producing culture grows most rapidly on malt extract agar and at temperatures of about 26° C. When the culture is inoculated in a 10-mm diameter area on malt extract agar, a colony up to 45 mm in diameter is produced in 3 days. This colony is enlarged to have a diameter of up to 65 mm after ten days.

When the culture is similarly inoculated on Czapek's solution agar, the colonies are more restricted. In three days the colonies are 27 mm in diameter with a 3-mm border of submerged colorless hyphae. In ten days the colonies are 50 mm in diameter.

Colonies on malt extract agar are zonate; colonies are Czapek's solution agar are azonate. Peripheries on both media are smooth to sinuate to crenate. On malt extract agar the colonies are slightly floccose and loosely textured. On Czapek's solution agar colonies range from lightly floccose to almost velutinous.

Color change is most striking on Czapek's solution agar. Young cultures range from near yellow to moderate yellow (ISCC-NBs87), quince yellow (M&P 11-L-3) in ten days. Cultures pass through the typical yellowish-green stage of the *A. flavus-oryzae* group to become moderate yellowish brown in 15 days. Older cultures advance to darker shades approaching brown. Reverse colors are colorless to yellowish white (ISCC-NBS 92), polar bear (M&P 9-A-2). On malt extract agar, colonies retain the typical yellowish-green color until 12 to 15 days when there is a tendency toward brown or dark bronze. *Czapek's Solution Agar*

Conidial heads vary widely in size and with age. They are loosely radiate and globose. They generaly are up to about 400 $\mu$ in diameter, although some are larger (possibly up to 500 $\mu$ in diameter).

Conidiophores are colorless, typically rough-walled, and frequently taper gently toward the vesicle. They arrange in length from 1.2 mm to 2.9 mm, averaging 1.9 mm. The apical vesicle is a fragile, colorless, thin-walled structure which tends to collapse when mounted. It is globose to subglobose to pyriform and is generally fertile over the entire free surface. Vesicles range in diameter from 38.8$\mu$ to 49.6$\mu$, averaging 47.5 $\mu$.

Conidia are conspicuously rough-walled, echinulate to verrucose. They are globose to subglobose and in strongly adherent chains. Young conidia are virtually hyaline, then become yellowish to brown. They range in size from 4.6 $\mu$ to 6.0$\mu$ in diameter with an average diameter of 5.25 $\mu$.

Sterigmata are frequently biseriate in larger heads and uniseriate in smaller heads. Primary sterigmata range from 8.7 $\mu$ to 12.6$\mu$ by 5.5$\mu$ to 6.3$\mu$. They are smooth-walled and colorless. Secondary sterigmata are adorned by a conspicuous collarette after 10 days. The opening is 8 $\mu$ in diameter, and the base is 4 $\mu$ in diameter. The collarette extends 4 $\mu$ beyond the main body of the conidiogenous cell, which is nearly oval. Excluding the collarette, the secondary sterigmata range from 15.8 $\mu$ to 23.7 $\mu$ long and 9.45 $\mu$ to 12.64 $\mu$ wide.

MALT EXTRACT AGAR

Conidiophores range from 300 $\mu$ to 700 $\mu$ in length and average 600 $\mu$. The globose, subglobose to pyriform vesicles are 26 $\mu \times$ 36 $\mu$ to 27 $\mu \times$ 29$\mu$ in diameter. Sterigmata are in single series. They seldom demonstrate the collarette. Sterigmata frequently cover only ⅔ of the vesicle surface. They range from 8 $\mu$ to 14$\mu$ by 4 $\mu$ to 8 $\mu$. Conidia are morphologically similar to those on Czapek's agar and range in size from 2.4 $\mu$ to 6.3 $\mu$ in diameter, averaging 5.5 $\mu$ in diameter.

The A-30641-producing culture strongly resembles *Aspergillus oryzae*. The tendency of this culture to assume a bronze pigmentation, however, is a characteristic used by Raper and Fennell, supra, to separate *A. tamarii* from *A. oryzae*. Other characteristics of the A-30641-producing culture, such as strongly verruculose conidia and the length of the conidiophores, tend to support the separation of *A. tamarii* from *A. oryzae*.

The yellow-green pigmentation in young cultures places the A-30641-producing culture in the *A. flavus-oryzae* form group.

The zonation of the A-30641-producing culture when grown on malt extract agar is similar to that of *A. zonatus*. The A-30641-producing culture, however, grows luxuriantly on Czapek's solution agar; whereas *A. zonatus* grows poorly on this medium with only a few conidial heads evident in up to two weeks.

Collarettes are not described for *A. tamarii* by Raper and Fennel, supra. Such collarettes were, however, observed to be present on two *A. tamarii* strains, QM Ob and QM 1223, from the Natick Culture Collection (University of Massachuseets, Amherst, Mass.). Both microscopic and macroscopic examination of these two strains tends to confirm the classification of the A-30641-producing culture as a strain of *Aspergillus tamarii Kita*.

The *Aspergillus tamarii* culture useful for the production of antibiotic A-30641 and canadensolide has been deposited and made a part of the stock culture collection of the Northern Regional Research Laboratory, Agricultural Research Service, U.S. Department of Agriculture, Peoria, Illinois, 61604, from which it is available to the public under the number NRRL 8101.

The culture medium employed to grow *Aspergillus tamarii* NRRL 8101 can be any one of a number of media. For economy in production, optimum yield and ease of product isolation, however, certain culture media are preferred. Thus, for example, a preferred carbohydrate source in large-scale fermentation is tapioca dextrin although sucrose, glucose, glycerol, corn starch, and the like can also be employed. A preferred nitrogen source is enzymatic hydrolysate of casein, although peptones such as soy peptone, corn steep liquor, amino acids, and the like are also useful.

Among the nutrient inorganic salts which can be incorporated in the culture media are the customary soluble salts capable of yielding sodium, magnesium calcium, ammonium, chloride, carbonate, sulfate, nitrate, and like ions.

Essential trace elements necessary for the growth and development of the organism should also be included in the culture medium. Such trace elements commonly occur as impurities in other constituents of the medium in amounts sufficient to meet the growth requirements of the organism.

It may be necessary to add small amounts (i.e. 0.2 ml/l. ) of an antiform agent such as polypropyleneglycol, to large-scale fermentation media if forming becomes a problem.

For production of substantial quantities of antibiotic A-30641 and canadensolide, submerged aerobic fermentation in tanks is preferred. Small quantities of these antibiotics may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The medium used for the growth of the vegetative inoculum can be the same as that employed for larger fermentation, but other media can also be employed.

The A-30641-producing organism can be grown at temperatures between about 18° and about 37° C. Optimum antibiotic production appears to occur at temperatures of about 25° C. Growth on agar media appears to occur best at temperatures of about 30°–34° C.

As is customary in aerobic submerged culture processes, sterile air is blown through the culture medium. For efficient growth of the organism the volume of air employed in tank production is preferably above 0.1 volume of air per volume of culture medium per minute. An especially preferred rate of aeration is 0.5 volumes of air per volume of culture medium per minute.

The initial pH of the uninoculated culture medium varies with the medium used. In general, the pH should be in the range of 6.0 to 7.0. The harvest pH at the end of the fermentation is usually slightly lower, in the range of 4.3 to 5.8.

The production of A-30641 and canadensolide can be followed during the fermentation by testing samples of the broth for antibiotic activity against organisms known to be sensitive to the antibiotics. One assay organism useful in testing for A-30641 is *Neurospora crassa*. *Bacillus subtilis* and *Klebsiella pneumoniae* are assay organisms useful in testing for both A-30641 and canadensolide. Bioassays are conveniently performed by paper-disc assay on agar plates.

Generally, antibiotic activity is detectable after the first day of the fermentation. Maximum production of antibiotic activity usually occurs about the second or third day.

Recovery of the A-30641 antibiotic complex comprising antibiotic A-30641 and canadensolide can be accomplished by methods generally employed in the fermentation art. The a-30641 antibiotic complex is present in both the filtered broth and the mycelial mass. The A-30641 antibiotic complex is conveniently separated from the filtered broth by acidifying the broth and separating the complex by adsorption or solvent-extraction techniques. The A-30641 antibiotic complex can be separated from the mycelial mass by extracting with methanol, concentrating the methanol extract under vacuum, acidifying the concentrated extract and extracting the acidified concentrate with a water-immiscible polar organic solvent. Chloroform is a preferred solvent, but other solvents such as ethyl acetate, methyl ethyl ketone, n-butanol and the like are also useful. Standard precipitation techniques assist in the further removal of fermentation impurities.

Individual antibiotic A-30641 and canadensolide are separated and isolated as individual compounds by additional adsorption procedures. Column chromatography over silica gel is an especially preferred procedure although other adsorbents such as carbon, alumina, and the like can be employed.

Under the conditions employed thus far, *Aspergillus tamarii* NRRL 8101 produces antibiotic A-30641 as the major metabolite. Although it is well known in the fermentation art that the ratio of metbolites produced will vary depending upon the fermentation conditions used, in general antibiotic A-30641 accounts for about 85% of the A-30641 antibiotic complex; canadensolide accounts for substantially all of the remaining 15% of the A-30641 antibiotic complex.

Antibiotic A-30641 inhibits the growth of bacteria and fungi which are pathogenic to animal and plant life. The minimal inhibitory concentrations (MIC's) at which antibiotic A-30641 inhibited a variety of organisms, using a standard agar-dilution assay, are summarized in Table III.

Table III

| Test Organism | MIC (mcg/ml) |
| --- | --- |
| *Staphylococcus aureus* 3055 | 3.12 |
| *Staphylococcus aureus* 3074 | 0.78 |
| *Streptococcus faecalis* X66 | >100 |
| *Proteus morganii* PR15 | >100 |
| *Salmonella typhosa* SA12 | >100 |
| *Klebsiella pneumoniae* KL14 | >100 |
| *Serratia marcescens* SE3 | >100 |
| *Escherichia coli* EC14 | >100 |
| *Citrobacter freundii* MX CF17 | >100 |
| *Pseudomonas aeruginosa* X239 | >100 |
| *Bordetella bronchiseptica* 16 | 50 |
| *Salmonella typhimurium* | >100 |
| *Pseudomonas solanacearum* X185 | >100 |
| *Erwinia amylovora* | 6.25 |
| *Candida tropicalis* Z17 | >100 |
| *Trichophyton mentagrophytes* 27 | 25 |
| *Aspergillus flavus* E | 25 |
| *Ceratocystis ulmi* | 12.5 |

Table III-continued

| Test Organism | MIC (mcg/ml) |
| --- | --- |
| *Cryptococcus neoformans* | <0.156 |
| *Blastomyces dermatitidis* | 10 |
| *Histoplasma capsulatum* | 10 |

Antibiotic A-30641 is especially useful as an antifungal agent. Using a standard disc-diffusion array, antibiotic A-30641 inhibited *Candida albicans* in amounts less than 0.312 mcg per disc.

The toxicity ($LD_{50}$) of antibiotic A-30641, when administered intraperitoneally to mice, was 106 mg/kg.

Antibiotic A-30641 is particularly useful when administered topically. For example, the lesions caused by a dermal *C. albicans* infection in rabbits were reduced in severity and size by treatment for ten days with a 1% solution of antibiotic A-30641 in propylene glycol.

Topical preparations of antibiotic A-30641 are adapted for administration to subjects exposed to, or infected with, sensitive bacteria or fungi. Suitable preparations include, for example, ointments, creams, emulsions, salves, emollients and sprays. Although the optimal concentrations will differ dependent upon variables such as the infecting bacteria or fungi, antibiotic A-30641 is typically effective in topical preparations in concentrations as low as 0.01 percent by weight.

In some instances, the A-30641 antibiotic complex can be employed without the necessity of separating the canadensolide, which is itself an antifungal agent. For example, in fighting fungal growth on environmental surfaces such as shower stalls, walls, floors, tables and the like, either the A-30641 antibiotic complex or the individual antibiotic A-30641 is suitable.

When used for such purposes, an effective amount of either the A-30641 antibiotic complex or individual antibiotic A30641 may be incorporated into various formulations, such as suspensions, emulsions, powders, dusts, soaps, detergents, aerosols and the like. Such preparations may be used for cleaning, disinfecting, or sterilizing. In such preparations either the A-30641 antibiotic complex or individual antibiotic A-30641 is typically effective in amounts as low as 0.05 percent by weight.

In order to illustrate more fully the operation of this invention, the following examples are provided.

EXAMPLE 1

A. Shake-flask Fermentation of *Aspergillus tamarii*

A culture of *Aspergillus tamarii* NRRL 8101 was prepared and maintained on an agar slant having the following composition (in deionized water).

| Ingredient | Percent |
| --- | --- |
| Glucose | 2.000 |
| Peptone* | 0.500 |
| $KH_2PO_4$ | 0.050 |
| $MgSO_4 . 7H_2O$ | 0.002 |
| $FeSO_4 . 7H_2O$ | 0.001 |
| Agar | 2.000 |
| Final pH 5.5 | |

*Bacto-Peptone, Difco Laboratories, Detroit, Mich.

The slant was inoculated with *Aspergillus tamarii* NRRL 8101, and the inoculated slant was incubated at 30° C. for seven days. The mature slant culture was covered with beef serum and scraped with a sterile loop to loosen the spores. The resulting beef-serum suspension of spores and mycelial fragments was lyophilized into six pellets.

One lyophilized pellet thus prepared was used to inoculate 50 ml of a vegetative medium having the following composition (in tap water):

| Ingredient | Percent |
| --- | --- |
| Glucose | 1.0 |
| Potato dextrin | 1.0 |
| Peptone* | 1.0 |
| Brewer's yeast fraction** | 0.5 |
| Final pH 0.2 | |

*Soy Peptone T, Sheffield Chemical Co., Norwich, N.Y.
**Amber BYF, Amber Laboratories, Juneau, Wisconsin The inoculated vegetative medium, in a 250 ml. wide-mouth Erlenmeyer flask, was incubated at 25° C. for 28 hours on a shaker rotating within a 5-cm circle at 250 rpm.

B. Tank Fermentation of Aspergillus tamarii

In order to provide a larger volume of inoculum, 20 ml of the incubated vegetative medium, prepared as described in Section A, was used to inoculate 400 ml of a second-stage vegetative growth medium having the same composition as that of the vegetative medium. This second-stage medium, in a 2-liter flask, was incubated at 25° C. for 24 hours on a shaker rotating within a 5-cm circle at 250 rpm.

This second-stage vegetative medium (1 liter) was used to inoculate 100 liters of sterile production medium of the following composition (in deionized water):

| Ingredient | Percent |
| --- | --- |
| Tapioca dextrin* | 4.00 |
| Enzymatic hydrolysate of Casein** | 1.00 |
| Blackstrap molasses | 1.00 |
| MgSO$_4$ . 7H$_2$O | 0.05 |
| CaCO$_3$ | 0.20 |

*Stadex No. 11, A. E. Staley Co., Decatur, Ill.
**NZ Amine A, Sheffield Chemical Co., Norwich, N.Y.

The medium was sterilized by autoclaving at 120° C. for about 30 minutes at about 15–20 pounds pressure. The inoculated production medium was allowed to ferment in a 165-liter conventional fermentation tank for 2 days at 25° C. The fermentation medium was aerated with sterile air and agitated by conventional means to provide a calculated oxygen-solution rate of 270 mcM/min.

EXAMPLE 2

Separation of the A-30641 Antibiotic Complex

Whole fermentation broth (95 l.) obtained as described in Example 1, was filtered with a filter aid (Hyflo Super-cel, a diatomaceous earth, Johns-Manville Products Corp.), using 3 g of filter aid per 100 ml of broth. The pH of the resulting filtered broth (75 l.) was adjusted to pH 3 by the addition of dilute sulfuric acid. The acidified broth was chromatographed on a column of adsorbent resin (Amberlite XAD-2, Rohm & Haas, Philadelphia, Pa. 19105). After washing the column first with water and then water:methanol (1:1), the fractions containing the A-30641 activity were eluted with methanol (100%).

The active fractions were combined and concentrated to an oil under vacuum. The oil thus obtained was dissolved in methanol (150 ml). The methanol solution was poured into a excess of diethyl ether (20 volumes). The precipitate which formed was separated and discarded. The supernatant was concentrated to an oil under vacuum. The oil thus obtained was dissolved in chloroform (150 ml), and this solution was poured into hexane (20 volumes). The precipitate which formed was separated and dried under vacuum to give 5.0 g of the A-30641 antibiotic complex.

EXAMPLE 3

Isolation of Antibiotic A-30641

A-30641 antibiotic complex, obtained as described in Example 2, was further purified by chromatography. The complex was dissolved in ethyl acetate (45 ml). This solution was diluted with benzene (400 ml). The resulting solution was placed on a 4.7- × 60-cm column of silica gel (Matheson, Coleman and Bell, Grade 62, 60-200 mesh). The column was first washed with benzene (5 l). Then canadensolide was eluted using (9:1) benzene-ethyl acetate (5 l.). These fractions were combined and concentrated under vacuum to give 328 mg of crude canadensolide as an oil.

Further elution of the column with (4:1) benzene-ethyl acetate gave the active fractions containing antibiotic A-30641. These active fractions were combined and concentrated under vacuum to give an oil. This oil was dissolved in chloroform (150 ml), and the chloroform solution was poured into hexane (3 l.). The white precipitate which formed was separated and dried under vacuum to give 2.1 g of antibiotic A-30641.

EXAMPLE 4

Purification of Canadensolide

The crude canadensolide (328 mg) obtained in Example 3, dissolved in benzene, was placed on a 40 g column of silica gel (E. Merck, Darmstadt, No. 60). Elution of the column was monitored by thin-layer chromatography on silica gel (Brinkman SGF plates), using a (1:1) benzene-ethyl acetate solvent system and detecting the canadensolide by short-wave UV light. Elution with benzene gave fractions containing canadensolide. These fractions were combined and evaporated under vacuum to give 211 mg of crystalline canadensolide, m.p. 43°–47° C.

EXAMPLE 5

Alternate Method for Separating the A-30641 Antibiotic Complex

Whole fermentation broth (96 l.), obtained as described in Example 1, was filtered with a filter aid (Hyflo Super-cel), using 2 g of filter aid per 100 ml of broth. The resulting filtered broth (80 l.) was adjusted to pH 3 by the addition of 5 N HCl. The acidified broth was extracted twice with 40 l. of chloroform. The chloroform extracts were combined and concentrated under vacuum to give the broth portion of the A-30641 antibiotic complex as an oily residue.

The separated mycelial cake obtained from filtration of the whole broth was extracted twice with 50 l. of methanol. The methanol extracts were combined and concentrated under vacuum to remove the methanol. The resulting aqueous concentrate was diluted to a volume of 40 l. by the addition of distilled water; this solution was adjusted to pH 3 by the addition of 5 HCl. The acidified solution was extracted twice with 20 l. of chloroform. The chloroform extracts were combined and concentrated under vacuum to give an oily residue. The residue thus obtained was dissolved in methanol (500 ml). this methanol solution was filtered to remove insoluble impurities; the filtrate was evaporated to dryness. The residue obtained was dissolved in 100 ml chloroform; the chloroform solution was added to hexane (2 l.) to precipitate the A-30641 antibiotic complex. The precipitate was separated by filtration, and dried under vacuum to give the mycelial portion (10.3 g.) of A-30641 antibiotic complex.

We claim:
1. Antibiotic A-30641 which has the probable formula:

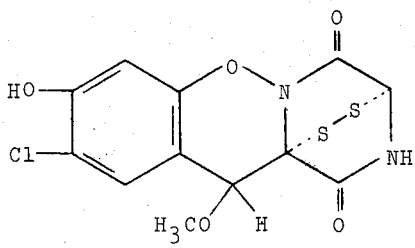

and which is an amorphous, colorless material which melts at about 160°–172° C. (decomp.);
and which has: an elemental composition of 40.29% carbon; 2.72% hydrogen; 7.67% nitrogen; 21.48% oxygen; 17.86% sulfur; and 9.54% chlorine; an empirical formula of $C_{12}H_9N_2O_5S_2Cl$; an apparent molecular weight of about 360; an infrared absorption spectrum in chloroform with the following significant absorption maxima; 3450 (OH), 1730 (>C=O), 1630 (amide), 1490, 1450, 1350, 1185, 1150 and 1050 $cm^{-1}$; a specific rotation of +73° ($c$=1, MeOH) when determined at a temperature of 26° C;
a proton magnetic resonance (pmr) spectrum is deuterated chloroform with the following characteristics: δ 3.95 (s), 4.88 (d, J = 1.2 Hz), 5.15 (d, J = 5 Hz), 6.20 (s, OH), 6.75 (s), 7.12 (d, J = 1.2 Hz), and 7.64 (d, J = 5 Hz) ppm; on $D_2O$ shake, the singlet at 6.20 and the doublet at 7.64 are lost; and the doublet at 5.15 becomes a singlet; and which gives the following fragments on high-resolution mass spectrometry:

| Elemental composition | Calcd. | Found |
|---|---|---|
| $C_{12}H_9N_2O_5S_2Cl$ | 359.9642 | 359.9670 |
| $C_{12}H_9N_2O_5Cl$ | 296.0200 | 296.0178 |
| $C_{10}H_8NO_4Cl$ | 241.0142 | 241.0138 |
| $C_{10}H_6N_2O_2Cl$ | 221.0118 | 221.0120 |
| $C_9H_4NO_3Cl$ | 208.9880 | 208.9890 |
| $C_8H_5NO_2Cl$ | 182.0008 | 182.0005 | which has the following $R_f$ values in the silica gel thin-layer chromatographic systems indicated below, using fluorescence quenching under short-wave ultraviolet light and iodine-azide spray for detection:

| Solvent System | $R_f$ |
|---|---|
| Benzene:ethyl acetate (1:1) | 0.31 |
| Chloroform:acetone (3:2) | 0.42 |
| Ethyl acetate:chloroform (3:1) | 0.39 | and the following $R_f$ values in the paper-chromatographic systems indicated below, using Klebsiella pneumoniae bioautography for detection:

| Solvent System | $R_f$ |
|---|---|
| Water saturated with butanol | 0.33 |
| Propanol:water (1:9) | 0.56 |
| Methanol:propanol:water (6:2:1) (paper buffered with 0.75 M $KH_2PO_4$ at pH 4.0) | 0.69 |
| Methyl ethyl ketone: benzene:$H_2O$ (1:5:1), upper layer | 0.83 |
| Methanol:0.05 M sodium citrate at pH 5.7 (7:3) (paper buffered with 0.05 M Na citrate at pH 5.7) | 0.76 | and which can be acetylated in a conventional manner to give an O-acetyl derivative which has an apparent molecular weight of 402, as determined by high-resolution mass spectrometry; and a pmr spectrum with all the characteristics of that of antibiotic A-30641 except for loss of the δ 6.20 ppm resonance and the addition of a resonance at Γ 2.34 ppm.

* * * * *